United States Patent
Liu et al.

(10) Patent No.: US 9,717,827 B2
(45) Date of Patent: Aug. 1, 2017

(54) IMMUNOMODULATORY MATERIALS FOR IMPLANTABLE MEDICAL DEVICES

(71) Applicant: The Regents of the University of California, Oakland, CA (US)

(72) Inventors: Wendy Liu, Irvine, CA (US); Yoon Kyung Kim, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/025,601

(22) Filed: Sep. 12, 2013

(65) Prior Publication Data

US 2014/0072603 A1    Mar. 13, 2014

Related U.S. Application Data

(60) Provisional application No. 61/700,196, filed on Sep. 12, 2012.

(51) Int. Cl.
| | |
|---|---|
| *A61L 31/16* | (2006.01) |
| *A61K 38/19* | (2006.01) |
| *A61K 47/42* | (2017.01) |
| *A61K 38/21* | (2006.01) |
| *A61K 38/17* | (2006.01) |
| *A61L 27/34* | (2006.01) |

(Continued)

(52) U.S. Cl.
CPC .......... *A61L 31/16* (2013.01); *A61K 38/1774* (2013.01); *A61K 38/191* (2013.01); *A61K 38/21* (2013.01); *A61K 38/212* (2013.01); *A61K 47/42* (2013.01); *A61L 17/005* (2013.01); *A61L 27/34* (2013.01); *A61L 27/54* (2013.01); *A61L 31/10* (2013.01); *A61L 2300/252* (2013.01); *A61L 2300/426* (2013.01); *A61L 2400/18* (2013.01)

(58) Field of Classification Search
CPC .... A61K 38/21; A61K 47/42; A61K 38/1774; A61K 38/191; A61K 38/212
See application file for complete search history.

(56) References Cited

U.S. PATENT DOCUMENTS

| | | |
|---|---|---|
| 8,333,959 B2 | 12/2012 | Kipp et al. |
| 8,986,736 B2 | 3/2015 | Rabinow et al. |

(Continued)

FOREIGN PATENT DOCUMENTS

WO    2011/010156 A1    1/2011

OTHER PUBLICATIONS

Andersson et al., Binding of a Model Regulator of Complement Activation (RCA) to a Biomaterial Surface: Surface-Bound Factor H Inhibits Complement Activation, Biomaterials (2001), pp. 2435-2443, 22.

(Continued)

*Primary Examiner* — Kyle Purdy
(74) *Attorney, Agent, or Firm* — Archer Norris, PLC; Sean D. Senn; Priti D. Phukan

(57) ABSTRACT

The present invention relates to biomaterials that interact with and regulate immune functions, as well as implantable materials and devices. In one embodiment, the present invention provides an implantable medical device comprising a biomaterial coated with one or more CD200 molecules. In another embodiment, the present invention provides a method of treating inflammation by administering a composition comprising one or more biomaterials that inhibit immune reactivity.

28 Claims, 9 Drawing Sheets

(51) Int. Cl.
A61L 27/54 (2006.01)
A61L 31/10 (2006.01)
A61L 17/00 (2006.01)

(56) References Cited

U.S. PATENT DOCUMENTS

2004/0214187 A1* 10/2004 Van Der Vuurst De Vries et al. ................................. 435/6
2005/0084456 A1* 4/2005 Tang et al. ...................... 424/46
2007/0275071 A1* 11/2007 Ensoli et al. ................. 424/489

OTHER PUBLICATIONS

Gorczynski et al., An Immunoadhesin Incorporating the Molecule OX-2 Is a Potent Immunosuppressant That Prolongs Allo- and Xenograft Survival, The Journal of Immunology (Aug. 1, 1999), pp. 1654-1660, 163(3).
Liu et al., CD200R1 Agonist Attenuates Mechanisms of Chronic Disease in a Murine Model of Multiple Sclerosis, The Journal of Neuroscience (Feb. 10, 2010), pp. 2025-2038, 30(6).
Simelyte et al., CD200-Fc, a Novel Antiarthritic Biologic Agent That Targets Proinflammatory Cytokine Expression in the Joints of Mice With Collagen-Induced Arthritis, Arthritis & Rheumatism (Apr. 2008), pp. 1038-1043, 58(4).
Stachelek et al., The Effect of CD47 Modified Polymer Surfaces in Inflammatory Cell Attachment and Activation, Biomaterials (2011), pp. 4317-4326, 32.
Wu et al., Protection of Nonself Surfaces from Complement Attack by Factor H-Binding Peptides: Implications for Therapeutic Medicine, The Journal of Immunology (Feb. 21, 2011), pp. 4269-4277, 186(7).

* cited by examiner

IMMUNOMODULATORY MATERIALS FOR IMPLANTABLE MEDICAL DEVICES

CROSS-REFERENCE TO RELATED APPLICATIONS

The present application claims the benefit of priority under 35 U.S.C. §119(e) of provisional application Ser. No. 61/700,196, filed Sep. 12, 2012, the contents of which are hereby incorporated by reference.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The host response to biomaterials is an enormous challenge for the design of medical devices. This response is characterized by the infiltration of inflammatory cells and their chronic activation, and often leads to the formation of a fibrous capsule. The capsule functions to isolate the foreign body from the host immune system, but is also detrimental to many devices including surgical devices, cardiovascular or orthopedic implants, engineered tissue constructs, and implanted biosensors. The dense, collagen-rich tissue may occlude blood vessels, or prevent diffusion of small molecules and nutrients to and from the implanted device. While current efforts to reduce the immune response to biomaterials have focused on passivating the surface to prevent adhesion of proteins and inflammatory cells, these approaches have not been sufficient in eliminating the foreign body response. Alternatively, materials have been impregnated with anti-inflammatory or anti-proliferative pharmacological agents (for example, in drug-eluting stents), but this strategy ultimately prevents healing around the device. Thus, there is a need in the art for novel and effective design of implantable devices.

SUMMARY OF THE INVENTION

Various embodiments include a method of diminishing immune reactivity of a biomaterial, comprising providing a biomaterial, and at least partially coating the biomaterial surface with CD200 molecules, or a pharmaceutical equivalent, derivative, analog and/or salt thereof. In another embodiment, the CD200 molecules are soluble recombinant CD200 protein. In another embodiment, the at least partially coated biomaterial surface suppresses immune cells. In another embodiment, the at least partially coated biomaterial surface suppresses macrophage activation and/or inflammation. In another embodiment, the at least partially coated biomaterial surface suppresses the release of reactive oxygen species (ROS). In another embodiment, the biomaterial is of polystyrene. In another embodiment, the biomaterial is a polystyrene microbead. In another embodiment, the biomaterial surface is coated at a CD200 density of 1 pmol (0.05 ug)/well. In another embodiment, the biomaterial surface is coated by CD200 using a non-site specific reaction between exposed amine groups of CD200 and a maleic-anhydride activated surface. In another embodiment, the biomaterial is implanted into a mammal. In another embodiment, the biomaterial is an implantable medical device. In another embodiment, the biomaterial is a surgical tool. In another embodiment, the biomaterial is a transplanted organ. In another embodiment, the CD200 molecules are conjugated to poly ethylene glycol (PEG) and/or poly lactic-co-glycolic acid (PLGA). In another embodiment, the CD200 molecules are conjugated to fibrin and/or collagen. In another embodiment, the CD200 molecules are conjugated to silicone, polyethylene, polyether ether ketone (PEEK), polymethylmethacrylate, and/or polytetrafluoroethylene (PTFE). In another embodiment, the biomaterial includes silicone, polyethylene, polyether ether ketone (PEEK), polymethylmethacrylate, and/or polytetrafluoroethylene (PTFE). In another embodiment, the biomaterial is made of metal and/or ceramic.

Other embodiments include a method of preparing a biomedical device, comprising: providing a biomedical device, and coating the biomedical device surface with a material designed to modulate immune response through molecular interactions with surface receptors expressed by immune cells. In another embodiment, the material comprises a plurality of CD200 molecules, or a pharmaceutical equivalent, derivative, analog and/or salt thereof. In another embodiment, the surface receptors expressed by immune cells are CD200R. In another embodiment, the biomedical device surface is polystyrene. In another embodiment, the biomedical device comprises silicone, polyethylene, polyether ether ketone (PEEK), polymethylmethacrylate, and/or polytetrafluoroethylene (PTFE).

Other embodiments include a composition comprising a biomaterial and one or more CD200 molecules, or a pharmaceutical equivalent, derivative, analog and/or salt thereof. In another embodiment, the composition is administered as part of an overall treatment regimen. In another embodiment, the biomaterial is a medical and/or implantable device. In another embodiment, the biomaterial is a therapeutic. In another embodiment, the biomaterial is a transplant organ.

Other embodiments include a medical device, comprising a medical device surface at least partially coated by one or more molecules that diminish immune reactivity. In another embodiment, the one or more molecules that diminish immune reactivity comprise CD200 molecules, or a pharmaceutical equivalent, derivative, analog and/or salt thereof. In another embodiment, the one or more molecules that diminish immune reactivity reduce inflammation and/or fibrosis that results from implantation. In another embodiment, the one or more molecules that diminish immune reactivity are conjugated to poly ethylene glycol (PEG) and/or poly lactic-co-glycolic acid (PLGA). In another embodiment, the one or more molecules that diminish immune reactivity are conjugated to fibrin and/or collagen. In another embodiment, the medical device surface comprises silicone, polyethylene, polyether ether ketone (PEEK), polymethylmethacrylate, and/or polytetrafluoroethylene (PTFE).

Various embodiments include a method of treating a subject, comprising providing a composition comprising a biomaterial and one or more CD200 molecules, and administering a therapeutically effective dosage to the subject. In another embodiment, administering the composition treats an inflammatory immune attack and/or an autoimmune condition in the subject. In another embodiment, administering the composition decreases scar tissue in the subject. In another embodiment, the one or more CD200 molecules are conjugated to poly ethylene glycol (PEG) and/or poly lactic-co-glycolic acid (PLGA). In another embodiment, the one or more CD200 molecules are conjugated to silicone, polyethylene, polyether ether ketone (PEEK), polymethylmethacrylate, and/or polytetrafluoroethylene (PTFE). In another embodiment, the one or more CD200 molecules are conjugated to fibrin and/or collagen.

Other features and advantages of the invention will become apparent from the following detailed description, taken in conjunction with the accompanying drawings, which illustrate, by way of example, various embodiments of the invention.

DESCRIPTION OF THE INVENTION

Figure 1:
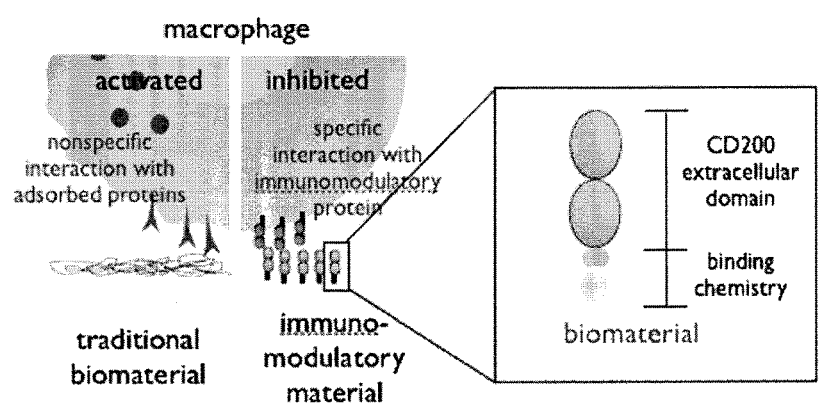
FIG. 1 depicts, in accordance with an embodiment herein, a schematic drawing demonstrating that where a traditional biomaterial becomes nonspecifically coated with interstitial or serum proteins upon implantation, ultimately leading to chronic macrophage inflammatory activation, immunomodulatory biomaterials are pre-coated with proteins that interact with receptors on immune cells and inhibit inflammatory activation. For example, the extracellular domain of CD200 is attached to a biomaterial surface through a chemical binding interaction.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3$^{rd}$ ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, the term "immunomodulatory molecule" refers to a molecule that may interact with and/or regulate immune cell function. For example, an immunomodulatory molecule may prevent inflammatory processes, or limit formation of scar tissue.

As used herein, "CD200" refers to the Cluster of Differentiation 200 protein.

As disclosed herein, the inventors leveraged natural interactions between immune cells and host organisms or foreign bodies, namely the ability to distinguish dangerous from non-dangerous, creating extremely biocompatible materials that can escape inflammatory immune attack. Recombinant protein methods along with bioconjugation strategies were used to tether immunomodulatory proteins to biomaterials. After coating materials with the immunomodulatory molecule CD200, the inventors successfully reduced adhesion and inflammatory activation of adhered immune cells.

In one embodiment, the present invention provides a biomaterial that reduces immune reactivity. In another embodiment, the biomaterial is part of a medical devices. In another embodiment, the medical device is implantable. In another embodiment, the biomaterial is used as a surgical tool. In another embodiment, the biomaterial is used in conjunction with organ transplants. In another embodiment, the biomaterial is at least partially coated by CD200 molecules. In another embodiment, the biomaterial reduces immune reactivity by suppressing macrophage activation and/or inflammation. In another embodiment, the biomaterial is made up of metal or ceramic. In another embodiment, the biomaterial is made up of one or more of the following: poly ethylene glycol (PEG), poly lactic-co-glycolic acid (PLGA), silicone, polyethylene, polyether ether ketone (PEEK), polymethylmethacrylate, and polytetrafluoroethylene (PTFE). In another embodiment, the CD200 molecules are conjugated to one or more of the following: poly ethylene glycol (PEG), poly lactic-co-glycolic acid (PLGA), silicone, polyethylene, polyether ether ketone (PEEK), polymethylmethacrylate, and polytetrafluoroethylene (PTFE).

In another embodiment, the present invention provides a method of diminishing immune reactivity of a biomaterial by at least partially coating the biomaterial with immunomodulatory molecules. In another embodiment, the present invention provides a method of diminishing immune reactivity of a biomaterial by at least partially coating the biomaterial with CD200 molecules. In another embodiment, the biomaterial reduces immune reactivity by suppressing macrophage activation and/or inflammation. In another embodiment, the biomaterial is made up of metal or ceramic. In another embodiment, the biomaterial is made up of one or more of the following: poly ethylene glycol (PEG), poly lactic-co-glycolic acid (PLGA), silicone, polyethylene, polyether ether ketone (PEEK), polymethylmethacrylate, and polytetrafluoroethylene (PTFE). In another embodiment, the CD200 molecules are conjugated to one or more of the following: poly ethylene glycol (PEG), poly lactic-co-glycolic acid (PLGA), silicone, polyethylene, polyether ether ketone (PEEK), polymethylmethacrylate, and polytetrafluoroethylene (PTFE).

In another embodiment, the present invention provides a composition comprising a biomaterial and one or more immunomodulatory molecules. In another embodiment, the immunomodulatory material includes CD200, or pharmaceutical equivalent, derivative, analog, or salt thereof. In another embodiment, the present invention provides a method of treating inflammatory immune attack and/or autoimmunity. In another embodiment, the biomaterial is made up of metal or ceramic. In another embodiment, the biomaterial is made up of one or more of the following: poly ethylene glycol (PEG), poly lactic-co-glycolic acid (PLGA), silicone, polyethylene, polyether ether ketone (PEEK), polymethylmethacrylate, and polytetrafluoroethylene (PTFE). In another embodiment, the CD200 molecules are conjugated to one or more of the following: poly ethylene glycol (PEG), poly lactic-co-glycolic acid (PLGA), silicone, polyethylene, polyether ether ketone (PEEK), polymethylmethacrylate, and polytetrafluoroethylene (PTFE).

As further disclosed herein, the inventors coated materials with molecules that can interact with and regulate immune cell function. These molecules are naturally expressed by host cells and can prevent spurious activation of immune cells against host tissue, and/or autoimmunity. By leveraging natural interactions between host tissue and immune cells, these materials can control immune cell activation and harness the patient's own regenerative potential to healthy tissue with minimal scarring around the implant material. In one embodiment, the present invention provides immunomodulatory materials that can control inflammatory processes and/or fibrosis associated with implantation of a foreign material. In another embodiment, the present invention improves the overall function of the device by limiting scar tissue. In another embodiment, biomaterials may be modified with immunomodulatory peptides and/or one or more small molecule agonists that confer inhibition of macrophages. In another embodiment, CD200 may be used in combination with one or more other immunomodulatory molecules or materials recognized by immune cells molecules to optimize the tissue response. As further disclosed herein, CD200 is highly expressed in the placenta which fosters immune tolerance at the fetal-maternal interface. In another embodiment, the present invention includes incorporating immunoregulatory features of the placenta to achieve immune tolerance.

The present invention is also directed to a kit for preparing immunomodulatory materials and biomaterials that reduce immune reactivity. For example, the kit is useful for practicing the inventive method of implantable biomaterials and devices. The kit is an assemblage of materials or components, including at least one of the inventive compositions. Thus, in some embodiments the kit contains a composition including biomaterials coated by CD200, or pharmaceutical equivalents, derivatives, analogs, and/or salts thereof, as described above.

The exact nature of the components configured in the inventive kit depends on its intended purpose. For example, some embodiments are configured for the purpose of treating and/or decreasing scar tissue. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to implant a medical device in a subject. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing one or more CD200 molecules with biomaterials. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Background of CD200

In one embodiment, the present invention leverages natural interactions between immune cells and host organisms or foreign bodies, namely the ability to distinguish "dangerous" from "non-dangerous". Biocompatible materials are created that can escape inflammatory immune attack. An important feature of the immune system is the ability to distinguish dangerous from non-dangerous substances, in order to specifically target infectious organisms while preventing damage to the host itself. Pathogens display molecular patterns that are recognized by specific receptors expressed by immune cells, the binding of which leads to cell activation. In contrast, host cells express surface receptors including CD200, CD47, or CD55 that specifically inhibit inappropriate inflammatory immune, thus resulting in prevention of deleterious spurious activation on self tissue. Immunoregulatory molecules play an important role in maintaining homeostasis and preventing immune hyperactivity, and defects in these molecules have been shown to lead to chronic inflammation and autoimmunity. CD200 is a surface glycoprotein that delivers inhibitory signals to immune cells including neutrophils and macrophages, and is expressed in many tissues including endothelium, neurons, and thymocytes. Notably, high levels of gene expression are found in the placenta which provides immune tolerance during pregnancy. Mice deficient in CD200 have increased numbers of infiltrating macrophages and are susceptible to autoimmune diseases and infections. Moreover, elevated expression of CD200 protects from inflammation-mediated neurodegeneration, and some cancers upregulate CD200 to escape immune attack.

Example 2

Immunomodulatory Biomaterial

Figure 2:
FIG. 2 depicts, in accordance with an embodiment herein, CD200-coated surfaces inhibit adhesion and spreading of inflammatory macrophage cells. Phase contrast images of macrophage cells seeded on polystyrene surfaces and CD200-coated polystyrene surfaces, with and without inflammatory (IFN-γ) stimuli.
Figure 3:
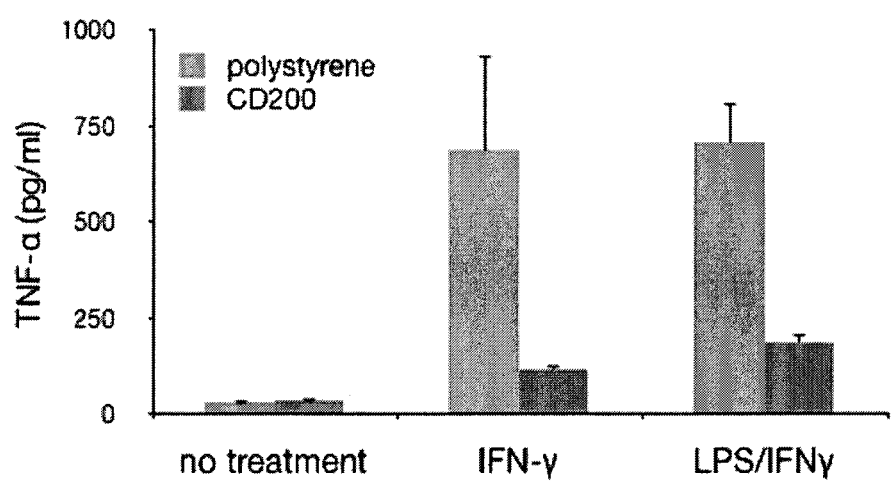
FIG. 3 depicts, in accordance with an embodiment herein, CD200-coated surfaces inhibit inflammatory activation of macrophage cells. Quantification of pro-inflammatory cytokine (TNF-α) secretion of macrophage cells seeded on CD200-coated (red) or polystyrene (blue) surfaces and stimulated with IFN-γ or LPS and IFN-γ (inflammatory stimuli) as indicated.

In one embodiment, the present invention provides an immunomodulatory biomaterial, whereby materials are designed to interact with specific receptors expressed on host immune cells, and modulate their activation. The inventors have demonstrated that coating materials with the immunomodulatory molecule CD200 reduces the adhesion and inflammatory activation of adhered immune cells (For example, FIG. 1-3). Biomaterials decorated with immunomodulatory molecules will reduce inflammatory cell activation and thus prevent the ensuing inflammation and fibrosis that results from material implantation. In addition, the effective domain of the immunomodulatory protein CD200 is located within a peptide region. Biomaterials may be modified with peptides, engineered peptide derivatives that have enhanced binding properties, or a small molecule agonist, that confers inhibition of macrophages. Moreover, CD200 is one of several immunomodulatory molecules recognized by immune cells, and materials combining other immunomodulators or combinations of molecules, may be used to optimize the tissue response. CD200 is highly expressed in the placenta, which fosters immune tolerance at the fetal-maternal interface. Thus, incorporating other immunoregulatory features of the placenta may be used to create an "artificial placenta" material to achieve immune tolerance.

Example 3

Method of Fabrication

Recombinant protein methods along with bioconjugation strategies are used to tether immunomodulatory proteins to biomaterials. To test our strategy, we cloned the extracellular domain of CD200 (Origene, Inc.) into pEE14 expression vector (University of Queensland) along with a His tag for purification and Avitag for site-specific biotinylation at the C-terminus. The resultant vector was then transfected into CHO.K1 cells (ATCC), which were then selected, expanded, and cultured in a chemically-defined media (Lonza) in order to minimize contaminating serum proteins in the cell culture supernatant. Secreted recombinant protein was collected and purified from cell culture supernatant using a nickel column, and then biotinylated using biotin ligase (Avidity, Inc.). Biotinylated CD200 protein was bound to streptavidin-modified polystyrene surfaces. This general approach can be used to tether CD200 or other immunomodulatory molecule to any biomaterial.

Peptide alternatives may also be used instead of full protein, in which case the peptide may be synthesized directly. In addition, while the inventors utilized biotin-streptavidin (noncovalent, but strong $K_d=10^{-15}$M) interaction to bind the extracellular domain of CD200 to material surfaces, covalent conjugation methods may also be used to increase stability of protein-modified surfaces. To accomplish this, bio-orthogonal click chemistries may be performed, for example using native chemical ligation to create alkyl-functionalized CD200, which can be reacted to an azide-modified biomaterial.

Example 4

Advantages

Traditional methods to reduce the foreign body response to biomaterials have focused on developing nonadhesive materials that prevent protein and cell binding, based on the notion that if interactions with immune cells are prevented, then the inflammatory cascade that follows will be attenuated. While this approach has had some success for materials administered into a fluid environment such as the bloodstream (for example, PEGylated drug delivery carriers), it has not been effective for materials implanted in a more static environment such as the tissue space. Alternative approaches to immune inhibition may utilize pharmacological agents, as has been introduced in the form of drug-eluting stents. However, this approach can inhibit healing and also induce cytotoxic effects in local tissue.

In contrast, in accordance with an embodiment herein, the inventors did not seek to inhibit protein adsorption, nor elute pharmacological agents, but instead utilized an endogenous protein expressed on host cells. Since CD200 is naturally expressed on cells to inhibit spurious and nonspecific inflammatory activation, there are less difficulties associated with cytotoxicity. Furthermore, expression of the receptor to CD200, CD200R is upregulated in macrophages polarized towards a pro-healing phenotype, so that CD200 ligation can in fact stimulate wound healing. Thus, this immunomodulatory material can leverage the healing potential of the host cells to regenerate healthy tissue in the region surrounding the implant.

Example 5

Applications

In accordance with various embodiments described herein, some applications of these materials include: (1) coating sutures or other surgical devices, particularly those used in skin tissue where visible scar formation is not desirable (2) materials for vascular devices including stents and vascular grafts where inflammation and fibrosis around the device can lead to vessel occlusion, (3) materials used for biosensors, device leads (pacemakers, neurostimulators, etc) or cell encapsulation devices, where transport of signals from the tissue to the device may be impeded by fibrotic scar, and (4) tissue engineering or regenerative medicine applications in which the immune response to implanted scaffolds may induce scar formation that limits integration of engineered tissue with the host, for example materials for spinal cord regeneration.

Example 6

Results

Figure 4:
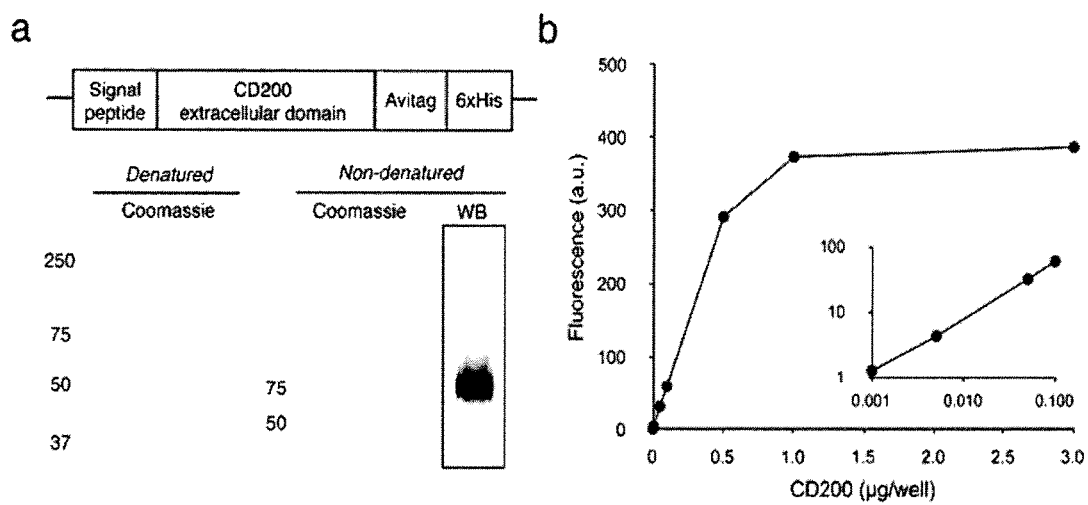
FIG. 4 depicts, in accordance with an embodiment herein, generation and characterization of CD200-modified surfaces. (a) Schematic of construct used for soluble expression of extracellular CD200 protein (top). Coomassie-blue stained SDS-PAGE (left) and native PAGE (middle) gels, and Western blot analysis (right) of purified recombinant CD200 product (bottom). (b) Binding profile of the CD200 immobilized on the streptavidin-coated polystyrene plate, measured with PE-labeled anti-mCD200.

The inventors show that immobilization of CD200, a potent ligand for active immunomodulation, onto a model biomaterial surface effectively inhibits material-induced host response. The inventors first generated soluble recombinant CD200 protein from mammalian CHO-K.1 cells transfected with plasmid DNA containing the extracellular region of CD200, AviTag sequence at the COOH terminus for site-specific biotinylation, and 6×His sequence for purification (FIG. 4a). Supernatant containing the secreted protein product was concentrated and purified, and then subjected to SDS- and native PAGE for characterization. A single band was observed in the Coomassie-stained gel at approximately 50 kDa (FIG. 4a), which was expected for the heavily glycosylated 25 kDa protein. The presence of protein was further confirmed by Western blot. The purified CD200 protein product was enzymatically biotinylated and then immobilized onto streptavidin-coated polystyrene surfaces.

To characterize the binding capacity of the surface, varying amounts of CD200-biotin were incubated in a streptavidin-coated polystyrene 96-well microplate for 2 h and rinsed. Immobilized CD200 was evaluated using a fluorescently labeled antibody directed against the extracellular domain of CD200. Measured fluorescence intensity linearly increased from 0.001 to 0.5 µg (0.02 to 10 pmol) of CD200 added to each well, and the surface was saturated with ~0.5-1 µg (10-20 pmol) of CD200 added to each well (FIG. 4b). The stability of the CD200-immobilized surfaces was assessed by characterizing changes in CD200 density on polystyrene surfaces incubated in PBS at 37° C. for two weeks after coating with 0.05 or 1 µg of CD200. The fluorescence intensity was measured after 0, 1, 3, 7, and 14 days, and showed no significant decrease in intensity, indicating that the immobilized CD200 remained stable for at least 2 weeks.

Figure 5:
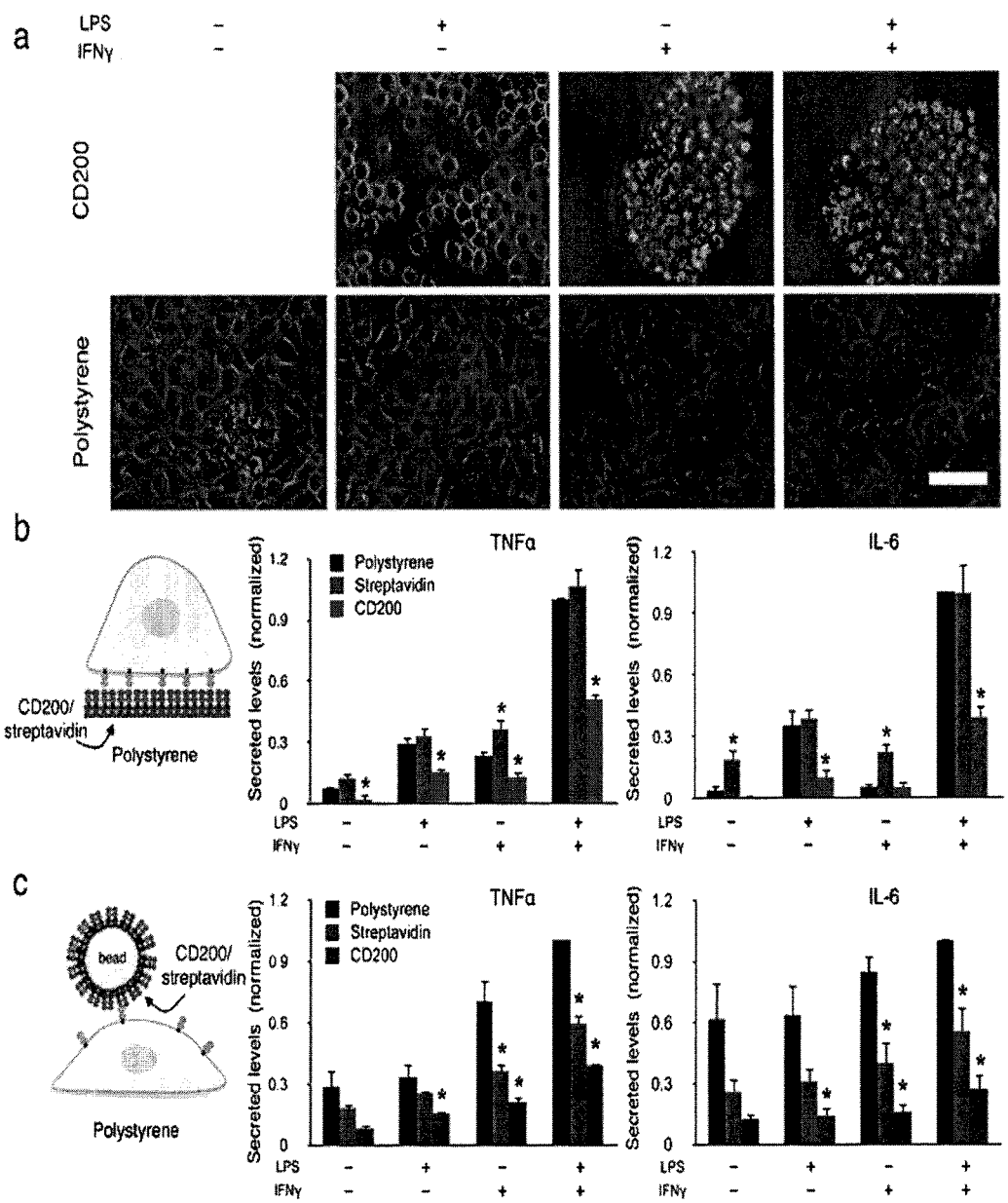
FIG. 5 depicts, in accordance with an embodiment herein, in vitro characterization of the inflammatory response to CD200-modified surfaces. (a) Representative phase contrast images of bone marrow derived macrophages seeded on mCD200-modified surfaces, or plain polystyrene surfaces, followed by stimulation with IFN-γ (0.5 ng/mL) and/or LPS (0.05 ng/mL). Scale bar 20 um. (b) Quantitative analysis of secreted pro-inflammatory cytokines (TNF-α and IL-6) by ELISA. CD200 immobilization on the polystyrene surface significantly inhibited macrophage activation with reduced level of pro-inflammatory cytokines. Secreted amounts were normalized to BMDM seeded on polystyrene and stimulated with IFN-γ and LPS. (c) Quantitative analysis of secreted pro-inflammatory cytokines (TNF-α and IL-6) of BMDMs incubated with CD200-coated, streptavidin-conjugated, and plain polystyrene 20-μm microbeads, and stimulated with IFN-γ and/or LPS. Secreted amounts were normalized to BMDM incubated with plain polystyrene microbeads and stimulated with IFN-γ and LPS. Error bars indicate standard error of the mean across three independent experiments. * $p<0.05$ compared to cells on polystyrene surfaces or treated with plain polystyrene beads, as determined by Student's t-test.

The immune-inhibitory properties of CD200-modified surfaces were evaluated in vitro by examining the response of bone-marrow derived macrophages (BMDM) seeded on the CD200-coated or plain polystyrene surface, followed by 18 hour stimulation with IFN-γ and/or LPS, potent stimulators of inflammation. The inventors found that modification of surfaces with CD200 caused the BMDM to have a more rounded morphology compared to cells on polystyrene, and that cells clustered together when IFN-γ was present (FIG. 5a). However, cells on the polystyrene surface were spread in all conditions, and dramatic differences were not observed between stimulated and unstimulated cells due to the confluency of the culture. The rounded morphology observed in cells cultured on CD200-modified surface suggests reduced macrophage inflammatory activation.

To assess macrophage activation, the release of pro-inflammatory cytokines, TNF-α and IL-6, was examined by ELISA. BMDM were seeded on CD200-coated surfaces, and streptavidin-coated and uncoated surfaces as controls, and stimulated with LPS and/or IFN-γ. It was found that cells seeded on CD200-coated wells exhibited lower secretion levels of both TNF-α and IL-6 (FIG. 5b), when compared to the control surfaces. In addition, IFN-γ and/or LPS induced secretion of TNF-α and IL-6 was also inhibited by the CD200-coated surface. These differences were not caused by changes in cell viability, since cells on CD200-coated and uncoated surfaces were all viable. The minimum concentration of CD200 coating density necessary to efficiently inhibit macrophage activation was 1 pmol (0.05 µg)/well. Moreover, the orientation of protein was important for the maximal inhibition of inflammation. Cells cultured on CD200 surfaces that were generated by a non-site specific reaction between exposed amine groups on the protein and a maleic-anhydride activated polystyrene surface exhibited greater levels of inflammatory cytokine secretion when compared to cells cultured on CD200-coated surface created using the biotin-streptavidin site-specific interaction.

The immunomodulatory effect of CD200 coating was confirmed using 20 µm diameter polystyrene microbeads as a base material, because this system could easily be tested in in vivo experiments. The inventors first assessed the materials in vitro by seeding BMDM on tissue culture polystyrene, and then adding CD200-coated, streptavidin-conjugated, or plain polystyrene microbeads to the cell culture medium, along with IFN-γ and/or LPS. Macrophages were the most highly activated in response to plain polystyrene beads, and activation was moderately reduced by coating the microbead surface with streptavidin. Only CD200-coated microbeads significantly inhibited macrophage activation, and reduced the level of secreted pro-inflammatory cytokines by greater than 70% in all conditions tested (FIG. 5c). This result demonstrated that the ligation of immobilized CD200 to CD200R on macrophages significantly suppressed their activation, while streptavidin only partially reduced macrophage activation.

Figure 6:
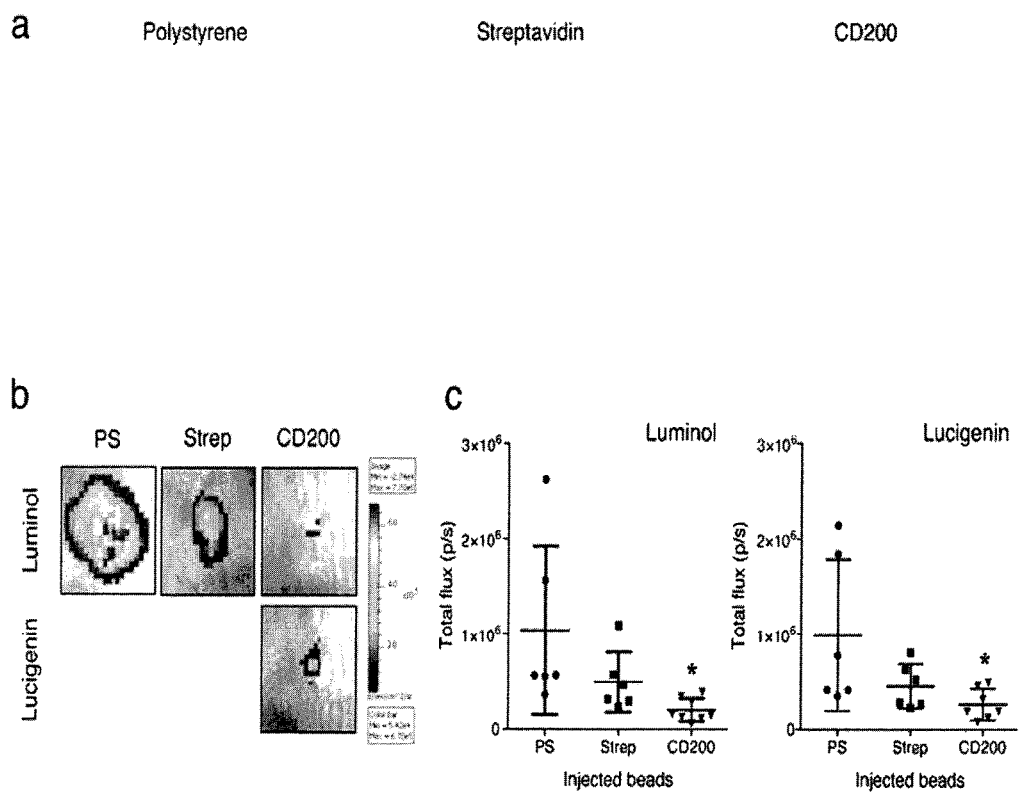
FIG. 6 depicts, in accordance with an embodiment herein, in vivo characterization of the inflammatory response to CD200-modified surfaces. (a) Representative sections of skin tissue containing subcutaneously injected CD200-coated, streptavidin-conjugated and plain polystyrene microbeads, stained with H&E. Scale bar 50 um. (b) Representative images of luminol and lucigenin bioluminescence generated at each injection site 1 day after microsphere implantation. (c) Quantification of total photon flux in at least 5 animals for each bead type. * $p<0.05$ compared to bioluminescence generated at plain polystyrene beads injection sites, as determined by Student's t-test.
Figure 7:
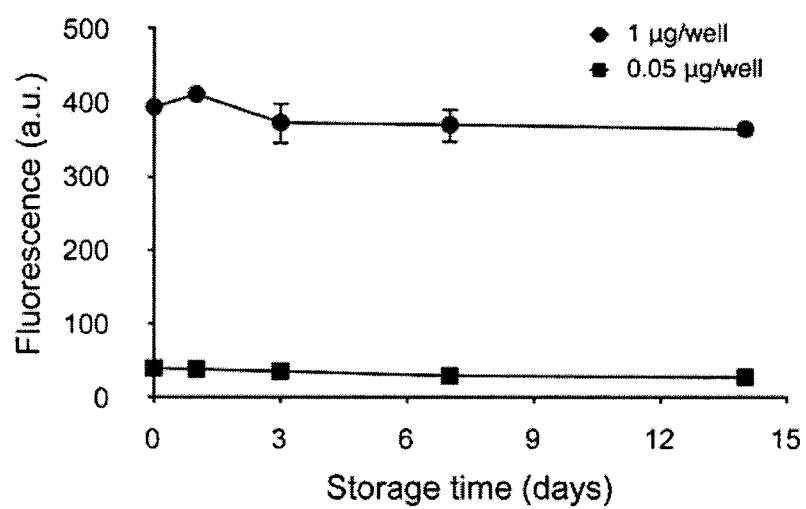
FIG. 7 depicts, in accordance with an embodiment herein, the stability of the CD200-modified surfaces generated with either 1 (●) or 0.05 μg (■) CD200/well and incubated in PBS at 37° C. for 14 days. Error bars indicate standard deviation of replicate wells.
Figure 8:
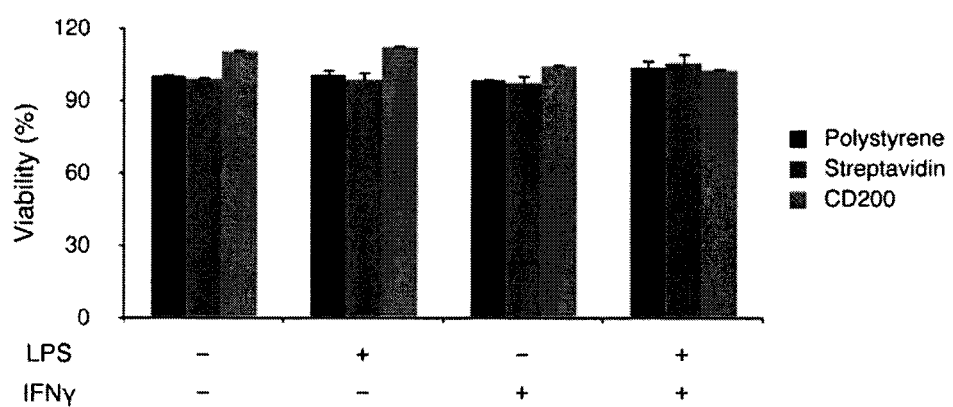
FIG. 8 depicts, in accordance with an embodiment herein, cell viability on the CD200-coated surface measured by MTS assay. Viability of BMDM incubated on CD200-coated, streptavidin, and plain polystyrene surfaces stimulated with IFN-γ (0.5 ng/mL) and/or LPS (0.05 ng/mL) for 18 h. Viability was normalized to cells on polystyrene without cytokine stimulation. Error bars indicate standard deviation of replicate wells.
Figure 9:
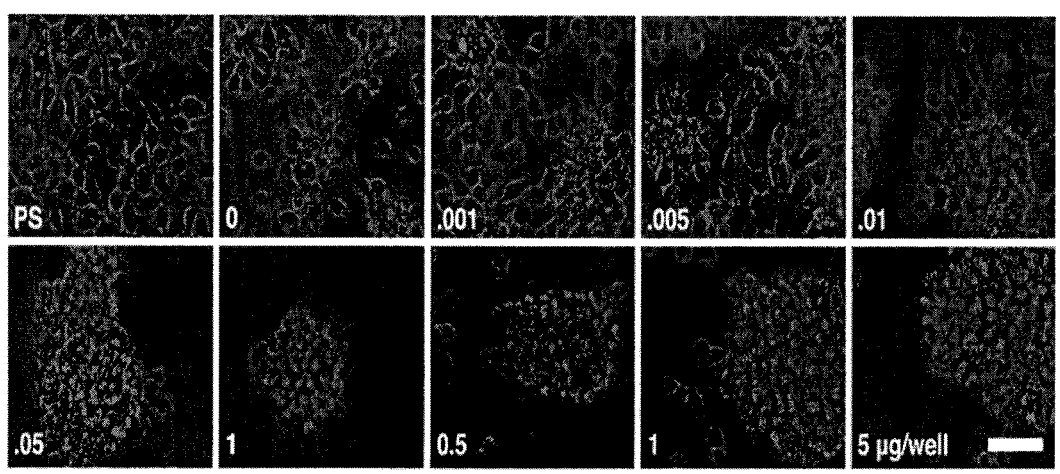
FIG. 9 depicts, in accordance with an embodiment herein, effect of CD200 coating density on macrophage morphology and activation. (a) Representative phase contrast images of BMDM cells seeded on CD200-coated surfaces with 0-5 ug of CD200-biotin/well concentrations, or plain polystyrene surface, followed by stimulation with IFN-γ (0.5 ng/mL). Scale bar 20 um. (b) Quantitative analysis of secreted TNF-α by ELISA. Secreted TNF-α amount was normalized to BMDM seeded on polystyrene and stimulated with IFN-γ. Error bars indicate standard error of three independent experiments.
Figure 9:
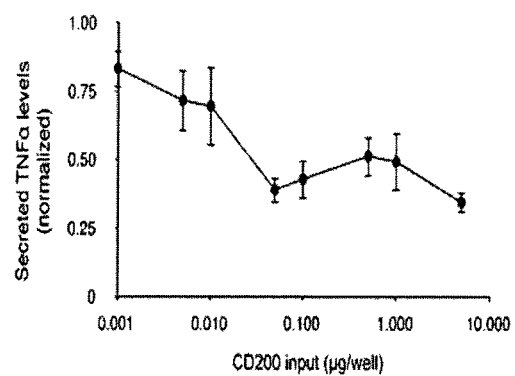
Figure 10:
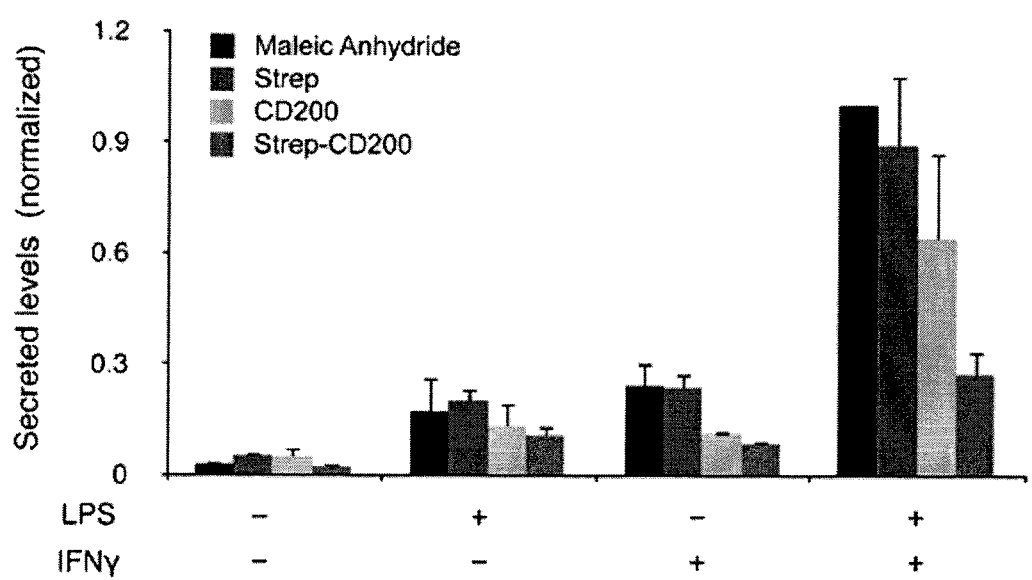
FIG. 10 depicts, in accordance with an embodiment herein, effect of binding orientation on immobilized CD200 activity. Secreted levels of TNF-α from BMDM seeded onto maleic anhydride functionalized polystyrene surfaces, or maleic anhydride functionalized surfaces conjugated with streptavidin, CD200, or streptavidin and biotinylated CD200, followed by stimulation with 0.5 ng/mL IFN-γ and/or 0.05 ng/mL LPS for 18 h. Error bars represent standard deviation of two independent experiments.

To evaluate whether CD200 provides a sufficient inhibitory signal to alleviate the foreign body response in vivo, the inventors next examined the effect of CD200 on the inflammatory response to materials subcutaneously injected into mice. CD200-coated, streptavidin-conjugated, and plain polystyrene microbeads were injected into the subcutaneous region on the dorsal side of C57BL/6 mice. Twenty-four hours after implantation, skin tissue containing the injected microbeads were retrieved, and stained with hematoxylin and eosin (H&E). Many infiltrated cells were observed in the tissue surrounding the plain polystyrene microbeads, whereas a moderate amount of infiltrated cells were found near streptavidin-conjugated microbeads, and even fewer inflammatory cells were present near CD200-coated microbeads (FIG. 6a). These data were well-correlated with levels of inflammatory cytokines released by macrophages after incubation with CD200-coated microbeads in vitro (FIG. 5c).

To assess the inflammatory response in a more quantitative manner, the inventors examined the release of reactive oxygen species (ROS) at the site of material implantation by bioluminescence imaging. Luminol (5-amino-2,3-dihydro-1,4-phthlazinedione) and lucigenin (bis-N-methylacridinium nitrate) were used as complementary probes to detect reactive oxygen species released by neutrophils and macrophages, respectively. Twenty-four hours after microbead injection, bioluminescent agents were administered and animals were imaged approximately 10-20 minutes afterwards, which was determined to be the timepoint for peak luminescence. Quantification of luminescence, or flux of photons, revealed that plain polystyrene microbeads induced the highest level of ROS, and CD200-coated microbeads elicited a significantly lower signal (FIGS. 6b and c). Modification with streptavidin, again, only moderately reduced ROS levels. These data further confirm the in vitro cytokine production and in vivo histological observations, and suggest that CD200 indeed lowers the level of inflammation when compared to uncoated or streptavidin-coated control microbeads.

This study provides critical evidence demonstrating that the immunomodulatory molecule, CD200, coated onto biomaterial surfaces functions to mitigate the inflammatory response. Importantly, the inventors observed an inhibitory effect using multiple in vitro and in vivo models. Thus, a new paradigm for materials used in biomedical implants, where materials are designed to actively modulate local immune response through specific molecular interactions with surface receptors expressed by immune cells. This strategy may also be explored for the delivery of nanotherapeutics. Translation of this technology will likely be enhanced by the discovery of small immunomodulatory molecules, for example a peptide fragment of CD200, which may have a similar inhibitory function to the full protein. In addition, there may also be covalent conjugation of CD200 to clinically relevant synthetic biomaterials such as PEG and PLGA, or natural biopolymers such as fibrin or collagen. Ultimately, the general strategy of coating biomaterials with immunomodulatory molecules to evade immune response to implanted materials may improve the efficacy of numerous medical devices.

Example 7

Generation of Recombinant mCD200 Protein

CD200-AviTag recombinant protein was constructed in the following order (N- to C-termini): the extracellular domain of mouse CD200 (GenBank Accession Number AAB93980; amino acids 1-232), a 15-amino acid stiff linker sequence (SLSTPPTPSPSTPPT), an AviTag amino acid sequence (GLNDIFEAQKIEWHE) for biotinylation, and a 6×His sequence for purification. The stiff linker-AviTag fragment was generated by high-temperature annealing, followed by primer extension. Plasmids encoding the extracellular domain of mCD200 (cDNA sequence 187-882) were PCR amplified using primers and PCR condition described in Supplementary Information. The constructed gene encoding (HindIII)-mCD200-(BamHI)-AviTag-6×His-stop-(XbaI) was transferred to a pEE14 expression vector (The University of Queensland, Brisbane, Australia). The final sequence of the gene was confirmed by DNA sequencing.

CHO-K.1 cells (ATCC, Manassas, Va.) were cultured according to published protocols and described in Supplemental Information. The cells were stably transfected with plasmid DNA of pEE14 vector containing mCD200-AviTag-6×His gene and the glutamine synthase minigene as a selectable marker, using lipofectamine LTX (Invitrogen) according to the manufacturer's instructions. Cells containing the transfected plasmid were selected in a glutamine-free culture media with 25-50 μM L-methionine sulfoximine (Sigma). Among ~10-15 colonies, a transfected CHO-K.1 cell line secreting the largest amount of mCD200-AviTag-6×His was determined by Western blot. Cells from the selected cell line were grown for 8 days in serum-free condition using chemically defined Pro CHO-AT media (Lonza, Verviers, Belgium) containing 1% HT supplement (Gibco). Supernatant containing CD200 protein was collected, filtered through a polyethylenesulfone 0.22-μm filter, and concentrated using a Pellicon XL Device and Labscale Tangential Flow Filtration system (Millipore). Concentrated supernatant was purified by applying to a HisTrap Ni column (GE healthcare, Uppsala, Sweden) at 4° C. Purified mCD200-AviTag protein was detected by Western blot after running the protein on native-PAGE, and further biotinylated by incubating with BirA enzyme at 30° C. for 2 h following the manufacturer's instructions (Avidity, Aurora, Colo.). Protein concentration was determined using μBCA Protein Assay Kit (Thermo Scientific, Rockford, Ill.). One liter of medium yielded approximately 1 mg of biotinylated mCD200. Purified protein contained less than 30 EU/mg protein, as determined by the *Limulus* Amebocyte Lysate gel clot endotoxin assay kit (GenScript, Piscataway, N.J.).

Example 8

Preparation of CD200-Coated Surfaces

Biotinylated CD200 was immobilized to streptavidin-coated 96-well plate (Thermo Scientific) at room temperature for 2 h under shaking, washed three times with Tris buffer containing 0.1% BSA and 0.05% Tween-20. The density of CD200 coated on the well was measured by incubating with a saturating concentration of PE-conjugated anti-mCD200 (rat IgG2a) (BioLegend) for 30 min at room temperature under agitation. Plates were washed thoroughly and incubated in PBS. The fluorescence intensity at 590 nm emission with 544 nm excitation was measured by a SpectraMax plate reader (Molecular Devices, Sunnyvale, Calif.).

To generate CD200-coated microspheres, 20 μm-diameter carboxyl-functionalized polystyrene microspheres were purchased from Bangs Laboratories (Fishers, Ind.), and streptavidin (Sigma) was conjugated onto microspheres using NHS and EDC coupling chemistry. 100 mg of carboxylated microspheres were sterilized in 70% ethanol, washed by centrifugation, and resuspended in activation buffer (100 mM MES, pH 5.5). 30 mg of 1-ethyl-aminopropyl-carbodiimide (EDC, Thermo Scientific) and 45 mg of N-hydroxysuccinimide (NHS, Thermo Scientific) were introduced simultaneously, and incubated for 15 min at room temperature with continuous mixing. Unreacted EDC and NHS were removed by several PBS washes, and the NHS-ester-modified microspheres were combined with 0.5 mg of streptavidin dissolved in PBS and mixed for 2 h at room temperature. Remaining active NHS esters were deactivated using 30 mM ethanolamine with 0.05% BSA, and streptavidin-coated microspheres were blocked with Superblock solution (Thermo Scientific) after several washes. Finally, biotinylated CD200 solution was added to streptavidin-conjugated microspheres.

Example 9

Macrophage Response In Vitro

Mouse C57BL/6 macrophage cells derived from bone marrow were cultured in DMEM (Gibco, Carlsbad, Calif.) supplemented with 10% heat-inactivated FCS, 2 mM L-glutamine, 10% M-CSF, 100 U/mL penicillin, and 100 μg/mL streptomycin. On day 7 of growth, cells were dislodged using cell-dissociation buffer (Gibco) after washing twice with Hank's Balanced Salt Solution (HBSS, Gibco). 1 μg of CD200-biotin per well was incubated in a streptavidin coated polystyrene microplate for 2 h at room temperature under shaking. After washing thoroughly with sterile PBS (Lonza), $1 \times 10^5$ of bone marrow macrophages were seeded on CD200-modified, streptavidin-coated, and plain polystyrene surfaces.

For incubation with CD200-coated microbeads, $1 \times 10^5$ macrophages were seeded into each well of a 96-well polystyrene tissue culture plate, and $8 \times 10^4$ plain polystyrene, streptavidin-conjugated, or CD200-coated microspheres were added 2 h later. After an additional 2 h, cells were stimulated with 0.5 ng/mL recombinant murine IFN-γ (R&D systems, Minneapolis, Minn.), and/or 0.05 ng/mL E. coli LPS (Sigma) for 18 h. Phase contrast images were acquired with an inverted microscope (Nikon Eclipse TE300) with a 20× objective to observe the cell morphology. Cell culture supernatants were collected and analyzed for secretion of pro-inflammatory cytokines, IL-6 and TNF-α, by enzyme-linked immunoabsorbent assay (ELISA) following the manufacturer's instructions (BioLegend, San Diego, Calif.). Student's t-test was performed to compare each condition with cells on plain polystyrene surfaces or treated with plain polystyrene beads, and $p < 0.05$ was considered statistically significant.

Example 10

Biomaterial Implantation, In Vivo Imaging and Histology

All procedures involving animals were performed in accordance with UC Irvine Institute for Animal Care and Use Committee (IACUC) approved protocols. 6-8 week-old female C57BL/6 mice (Jackson Laboratories, Sacramento, Calif.) were anesthetized by 2-3% isoflurane inhalation. CD200-coated microbeads, streptavidin-conjugated, and plain polystyrene microbeads were injected subcutaneously on the dorsal side of mice after removal of hair and disinfecting the skin surface. Each injection contained 100 μL of 20% (w/v) particle suspension in PBS. For tissue harvest and histology processing, mice were euthanized and skin samples containing the injected microparticles were excised and fixed in 10% formalin solution, embedded in paraffin blocks, sectioned and stained with hematoxylin and eosin (H&E) by AML Laboratories (Baltimore, Md.). The histology slides were imaged using a microscope (Nikon Eclipse E800) equipped with a 40× objective and an Olympus camera.

For luminol and lucigenin bioluminescence imaging, 50 mg/mL of luminol (Alfa Aesar, Ward Hill, Mass.) and 5 mg/mL of lucigenin (Sigma) stock solutions were prepared in sterile PBS prior to injection. Solutions (100 μL) were i.p. injected into mice, and animals were imaged using the IVIS imaging system (Caliper Life Sciences, Hopkinton, Mass.) approximately 10-20 minutes after luminol/lucigenin injection and using a 1 min exposure time. The images were analyzed with Living Image software (Caliper Life Sciences) and the total photon flux was quantified for each bead type. Student's t-test was performed to compare with bioluminescence generated at plain polystyrene beads injection sites and $p < 0.05$ was considered statistically significant.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of diminishing immune reactivity of a biomaterial, comprising:
   providing a biomaterial; and
   diminishing immune reactivity of the biomaterial by at least partially coating the biomaterial surface with CD200 molecules,
   wherein the biomaterial is an implantable medical device;
   wherein the concentration of the CD200 is at least 10 pmol; and
   wherein the CD200 is coated on the biomaterial using a biotin-streptavidin site-specific interaction.

2. The method of claim 1, wherein the CD200 molecules are soluble recombinant CD200 protein.

3. The method of claim 1, wherein the at least partially coated biomaterial surface suppresses immune cells.

4. The method of claim 1, wherein the at least partially coated biomaterial surface suppresses macrophage activation and/or inflammation.

5. The method of claim 1, wherein the at least partially coated biomaterial surface suppresses the release of reactive oxygen species (ROS).

6. The method of claim 1, wherein the biomaterial is of polystyrene.

7. The method of claim 1, wherein the biomaterial is a polystyrene microbead.

8. The method of claim 1, wherein the biomaterial surface is coated by CD200 using a non-site specific reaction between exposed amine groups of CD200 and a maleic-anhydride activated surface.

9. The method of claim 1, wherein the biomaterial is implanted into a mammal.

10. The method of claim 1, wherein the CD200 molecules are conjugated to poly ethylene glycol (PEG) and/or poly lactic-co-glycolic acid (PLGA).

11. The method of claim 1, wherein the biomaterial includes silicone, polyethylene, polyether ether ketone (PEEK), polymethylmethacrylate, and/or polytetrafluoroethylene (PTFE).

12. The method of claim 1, wherein the biomaterial is made of metal and/or ceramic.

13. A method of preparing a biomedical device, comprising:
   providing a biomedical device;
   coating the biomedical device surface with a material designed to modulate immune response through molecular interactions with surface receptors expressed by immune cells,
   wherein the biomedical device is implantable;

wherein the concentration of the CD200 is at least 10 pmol; and wherein the CD200 is coated on the biomaterial using a biotin-streptavidin site-specific interaction.

14. The method of claim 13, wherein the material comprises a plurality of CD200 molecules.

15. The method of claim 13, wherein the surface receptors expressed by immune cells are CD200R.

16. The method of claim 13, wherein the biomedical device surface is polystyrene.

17. The method of claim 13, wherein the biomedical device comprises silicone, polyethylene, polyether ether ketone (PEEK), polymethylmethacrylate, and/or polytetrafluoroethylene (PTFE).

18. A composition comprising a biomaterial and one or more CD200 molecules, wherein the biomaterial is an implantable medical device;

wherein the concentration of the CD200 is at least 10 pmol; and wherein the CD200 is coated on the biomaterial using a biotin-streptavidin site-specific interaction.

19. The composition of claim 18, wherein the composition is administered as part of an overall treatment regimen.

20. A medical device, comprising a medical device surface at least partially coated by one or more molecules that diminish immune reactivity, wherein the medical device is implantable;

wherein the concentration of the CD200 is at least 10 pmol; and wherein the CD200 is coated on the biomaterial using a biotin-streptavidin site-specific interaction.

21. The medical device of claim 20, wherein the one or more molecules that diminish immune reactivity comprise CD200 molecules.

22. The medical device of claim 20, wherein the one or more molecules that diminish immune reactivity reduce inflammation and/or fibrosis that results from implantation.

23. The method of claim 20, wherein the one or more molecules that diminish immune reactivity are conjugated to poly ethylene glycol (PEG) and/or poly lactic-co-glycolic acid (PLGA).

24. The method of claim 20, wherein the medical device surface comprises silicone, polyethylene, polyether ether ketone (PEEK), polymethylmethacrylate, and/or polytetrafluoroethylene (PTFE).

25. A method of treating a subject, comprising:
providing a composition comprising a biomaterial and one or more CD200 molecules; and
administering a therapeutically effective dosage to the subject,
wherein the biomaterial is an implantable medical device,
wherein the concentration of the CD200 is at least 10 pmol; and
wherein the CD200 is coated on the biomaterial using a biotin-streptavidin site-specific interaction.

26. The method of claim 25, wherein administering the composition treats an inflammatory immune attack and/or an autoimmune condition in the subject.

27. The method of claim 25, wherein administering the composition decreases scar tissue in the subject.

28. The method of claim 25, wherein the one or more CD200 molecules are conjugated to poly ethylene glycol (PEG) and/or poly lactic-co-glycolic acid (PLGA).

* * * * *